(12) United States Patent
Rapaka et al.

(10) Patent No.: US 11,127,138 B2
(45) Date of Patent: Sep. 21, 2021

(54) AUTOMATIC DETECTION AND QUANTIFICATION OF THE AORTA FROM MEDICAL IMAGES

(71) Applicant: Siemens Healthcare GmbH, Erlangen (DE)

(72) Inventors: Saikiran Rapaka, Pennington, NJ (US); Mehmet Akif Gulsun, Princeton, NJ (US); Dominik Neumann, Erlangen (DE); Jonathan Sperl, Bamberg (DE); Rainer Kaergel, Forchheim (DE); Bogdan Georgescu, Plainsboro, NJ (US); Puneet Sharma, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 61 days.

(21) Appl. No.: 16/196,454

(22) Filed: Nov. 20, 2018

(65) Prior Publication Data

US 2020/0160527 A1 May 21, 2020

(51) Int. Cl.
*G06T 7/11* (2017.01)
*G16H 30/40* (2018.01)
*G06K 9/46* (2006.01)
*G06T 7/00* (2017.01)
*G06T 7/12* (2017.01)

(52) U.S. Cl.
CPC .............. *G06T 7/11* (2017.01); *G06K 9/4638* (2013.01); *G06T 7/0012* (2013.01); *G16H 30/40* (2018.01); *G06K 2209/051* (2013.01); *G06T 7/12* (2017.01); *G06T 2200/04* (2013.01); *G06T 2207/10081* (2013.01); *G06T 2207/30101* (2013.01)

(58) Field of Classification Search
CPC .............................. G06T 19/20; G06T 19/003
USPC ........ 382/130, 128, 131, 173; 600/443, 301, 600/438, 437, 454
See application file for complete search history.

(56) References Cited

U.S. PATENT DOCUMENTS

| | | | |
|---|---|---|---|
| 9,715,637 B2 | 7/2017 | Zheng et al. | |
| 2004/0054280 A1 | 3/2004 | McMorrow et al. | |
| 2006/0280351 A1* | 12/2006 | Luping | G06K 9/00201 382/128 |
| 2008/0033302 A1 | 2/2008 | Grady et al. | |
| 2010/0296709 A1* | 11/2010 | Ostrovsky-Berman | G06T 7/11 382/128 |
| 2015/0005636 A1* | 1/2015 | Grisan | G06T 7/0012 600/443 |

(Continued)

OTHER PUBLICATIONS

Zheng et al., "Automatic Aorta Segmentation and Valve Landmark Detection in C-Arm CT for Transcatheter Aortic Valve Implantation", IEEE Transactions on Medical Imaging, vol. 31, No. 12, Dec. 2012, pp. 2307-2321.

(Continued)

*Primary Examiner* — Kiet M Doan (57) ABSTRACT

Systems and methods are provided for evaluating an aorta of a patient. A medical image of an aorta of a patient is received. The aorta is segmented from the medical image. One or more measurement planes are identified on the segmented aorta. At least one measurement is calculated at each of the one or more measurement planes. The aorta of the patient is evaluated based on the at least one measurement calculated at each of the one or more measurement planes.

14 Claims, 7 Drawing Sheets

(56) References Cited

U.S. PATENT DOCUMENTS

2016/0104281 A1* 4/2016 Grady .................. G06T 19/00
                                                        382/128
2018/0144219 A1* 5/2018 Kalisman ........... G06K 15/1848
2018/0303405 A1* 10/2018 Dugan .................. G16H 40/63
2019/0087957 A1* 3/2019 Burris .................... G16H 50/50

OTHER PUBLICATIONS

Yang et al., "Automatic Liver Segmentation Using an Adversarial Image-to-Image Network", International Conference on Medical Image Computing and Computer-Assisted Intervention, Springer, Cham, Jul. 25, 2017, 8 pgs.

Ronneberger et al., "U-Net: Convolutional Networks for Biomedical Image Segmentation", International Conference on Medical Image Computing and Computer-Assisted Intervention, May 18, 2015, Springer Cham, 8 pgs.

European Search Report dated Feb. 2, 2020 in corresponding European Patent Application No. 19210439.6.

Kurugol Sila et al.; "Automated quantitative 3D analysis of aorta size, morphology and mural calcification distributions"; Sep. 1, 2015; Medical Physics, AIP, Melville, NY, US; vol. 42; No. 9; pp. 5467-5478.

Extended European Search Report (EESR) dated Sep. 7, 2020 in corresponding European Patent Application Mo 19210439.6.

Erbel, et al.; "Aortic dimensions and the risk of dissection"; Heart; vol. 92, No. 1; Jan. 1, 2006; pp. 137-142.

Office Action dated Apr. 29, 2021 in corresponding European Patent Application No. 19210439.6.

Bai Wenjia et al: "Recurrent Neutral Networks for Aortic Image Sequence Segmentation with Sparse Annotations"; Sep. 13, 2018 (Sep. 13, 2018); ICIAP: International Conference on Image Analysis and Processing; 17th International Conference, Naples, Italy, Sep. 9-13, 2013 Proceedings; (Lecture Notes in Computer Science; Lect. Notes Computer); Springer, Berlin, Heidelberg; pp. 586-594.

* cited by examiner

Receive a medical image of an aorta of a patient
302

Segment the aorta from the medical image
304

Identify one or more measurement planes on the segmented aorta
306

Calculate at least one measurement at each of the one or more measurement planes
308

Evaluate the aorta of the patient based on the at least one measurement calculated at each of the one or more measurement planes
310

Generate an output based on the at least one measurement and/or results of the evaluation
312

AUTOMATIC DETECTION AND QUANTIFICATION OF THE AORTA FROM MEDICAL IMAGES

TECHNICAL FIELD

The present invention relates generally to detection and quantification of an aorta of a patient from medical images, and more particularly to the automatic detection and quantification of the aorta using a plurality of machine learning models to analyze medical images.

BACKGROUND

Early detection is critical for many aortic diseases, such as aortic dissection, aortic rupture, and ruptured abdominal aortic aneurysms. Left untreated, such aortic diseases have severe and potentially fatal consequences. Conventionally, such aortic diseases are diagnosed by manual evaluation of medical images of a patient. However, such aortic diseases are often asymptomatic and are only detected after complications have manifested. It is therefore difficult to diagnose such aortic diseases before complications have manifested, resulting in a delayed diagnosis or a failure to diagnose.

BRIEF SUMMARY OF THE INVENTION

In accordance with one or more embodiments, systems and methods are provided for evaluating an aorta of a patient. A medical image of an aorta of a patient is received and the aorta is segmented from the medical image. A measurement plane is identified on the segmented aorta and a measurement is calculated at the measurement plane. The aorta of the patient is evaluated based on the measurement calculated at the measurement plane. Results of the calculated measurement and/or the evaluated aorta may be caused to be displayed to a user on a display device. Advantageously, the embodiments described herein provide for the automatic detection and quantification of the aorta by applying machine learning models to medical images, even if such medical images were not acquired to diagnose aortic diseases.

In accordance with one or more embodiments, the measurement plane is identified on the segmented aorta by identifying an aortic centerline of the aorta and identifying a location on the aortic centerline and a corresponding plane normal vector as the measurement plane. The segmented aorta and the aortic centerline may be jointly and iteratively determined by refining the segmented aorta based on the aortic centerline and refining the aortic centerline based on the refined segmented aorta.

In accordance with one or more embodiments, the measurement calculated at the measurement plane is a diameter of the segmented aorta at the measurement plane. For example, the diameter may include a minimum diameter, a maximum diameter, and/or an average diameter of the segmented aorta at the measurement plane.

In accordance with one or more embodiments, the aorta of the patient is evaluated by comparing the measurement calculated at the measurement plane with a patient-specific range. An alert may be generated indicating results of the evaluating in response to the comparing. A risk score may also be calculated in response to the comparing and a clinical treatment plan may be caused to be presented to a user based on the risk score.

In accordance with one or more embodiments, an apparatus is provided for evaluating an aorta of a patient. The apparatus comprises means for receiving a medical image of an aorta of a patient, means for segmenting the aorta from the medical image, means for identifying one or more measurement planes on the segmented aorta, means for calculating at least one measurement at each of the one or more measurement planes; and means for evaluating the aorta of the patient based on the at least one measurement calculated at each of the one or more measurement planes.

In accordance with one or more embodiments, a non-transitory computer readable medium is provided. The non-transitory computer readable medium stores computer program instructions for evaluating an aorta of a patient. The computer program instructions when executed by a processor cause the processor to perform operations of receiving a medical image of an aorta of a patient, segmenting the aorta from the medical image, identifying one or more measurement planes on the segmented aorta, calculating at least one measurement at each of the one or more measurement planes, and evaluating the aorta of the patient based on the at least one measurement calculated at each of the one or more measurement planes.

These and other advantages of the invention will be apparent to those of ordinary skill in the art by reference to the following detailed description and the accompanying drawings.

DETAILED DESCRIPTION

The present invention generally relates to methods and systems for the automatic detection and quantification of the aorta from medical images. Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed by a computer system using data stored within the computer system.

Figure 1:
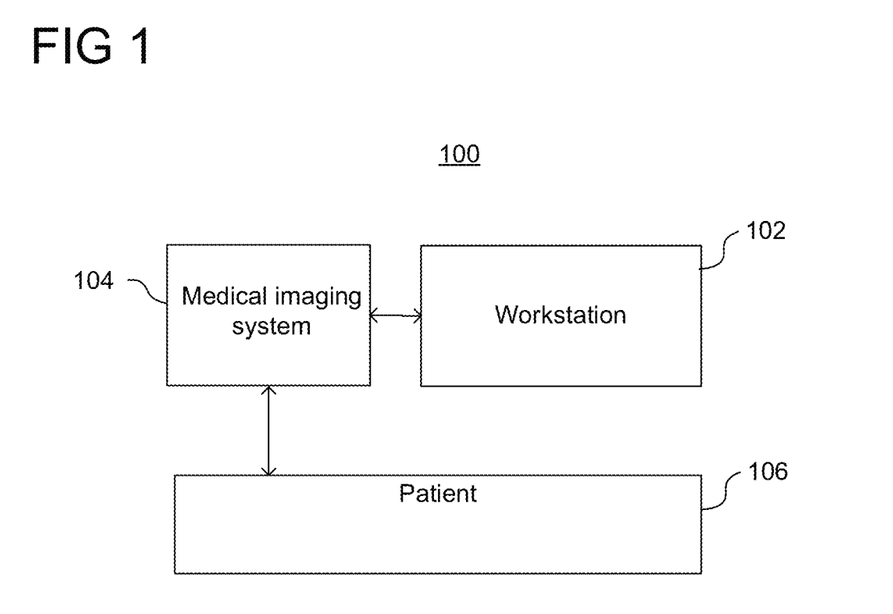
FIG. 1 shows an illustrative system for evaluating an aorta of a patient, in accordance with one or more embodiments.

FIG. 1 shows a system 100 configured to evaluate an aorta of a patient, in accordance with one or more embodiments. System 100 includes workstation 102, which may be used for assisting a clinician (e.g., a doctor, a medical professional, or any other user) in performing a medical evaluation of a patient 106 (or any other subject). Workstation 102 may be implemented using any suitable computing device, such as, e.g., computer 702 of FIG. 7.

In one embodiment, workstation 102 may assist the clinician in performing a medical evaluation of patient 106. The medical evaluation of patient 106 may be any medical evaluation of patient 106, including an evaluation related to a diagnosis of aortic diseases of patient 106 or an evaluation unrelated to a diagnosis of aortic diseases of patient 106. Accordingly, workstation 102 may receive medical images of patient 106 from one or more medical imaging systems 104. Medical imaging system 104 may be of any modality, such as, e.g., a two-dimensional (2D) or three-dimensional (3D) computed tomography (CT), x-ray, magnetic resonance imaging (MRI), ultrasound (US), single-photon emission computed tomography (SPECT), positron emission tomography (PET), or any other suitable modality or combination of modalities. In another embodiment, workstation 102 may receive the images by loading previously stored images of the patient acquired using medical imaging system 104.

Embodiments of the present invention provide for the automatic detection and quantification of the aorta of patient 106 by applying a plurality of machine learning models to analyze medical images. Advantageously, embodiments of the present invention enable fast and automatic analysis of medical images to evaluate aortic diseases of patient 106 and provide early detection of aortic diseases before symptoms or complications manifest. Such fast and automatic analysis allows for the analysis of routine medical images acquired while performing a medical evaluation unrelated to the diagnosis of aortic diseases of patient 106. Accordingly, while conventional, manual analysis of such medical images acquired for a medical evaluation unrelated to aortic diseases cannot practically be performed, embodiments of the present invention provide for fast and automatic analysis of medical images, thereby providing for an improvement in computers and computer related technology.

It should be understood that while the embodiments discussed herein may be described with respect to analyzing medical images to evaluate aortic diseases of a patient, the present invention is not so limited. Embodiments of the present invention may be applied for analyzing any type of image for any measure of interest.

Figure 2:
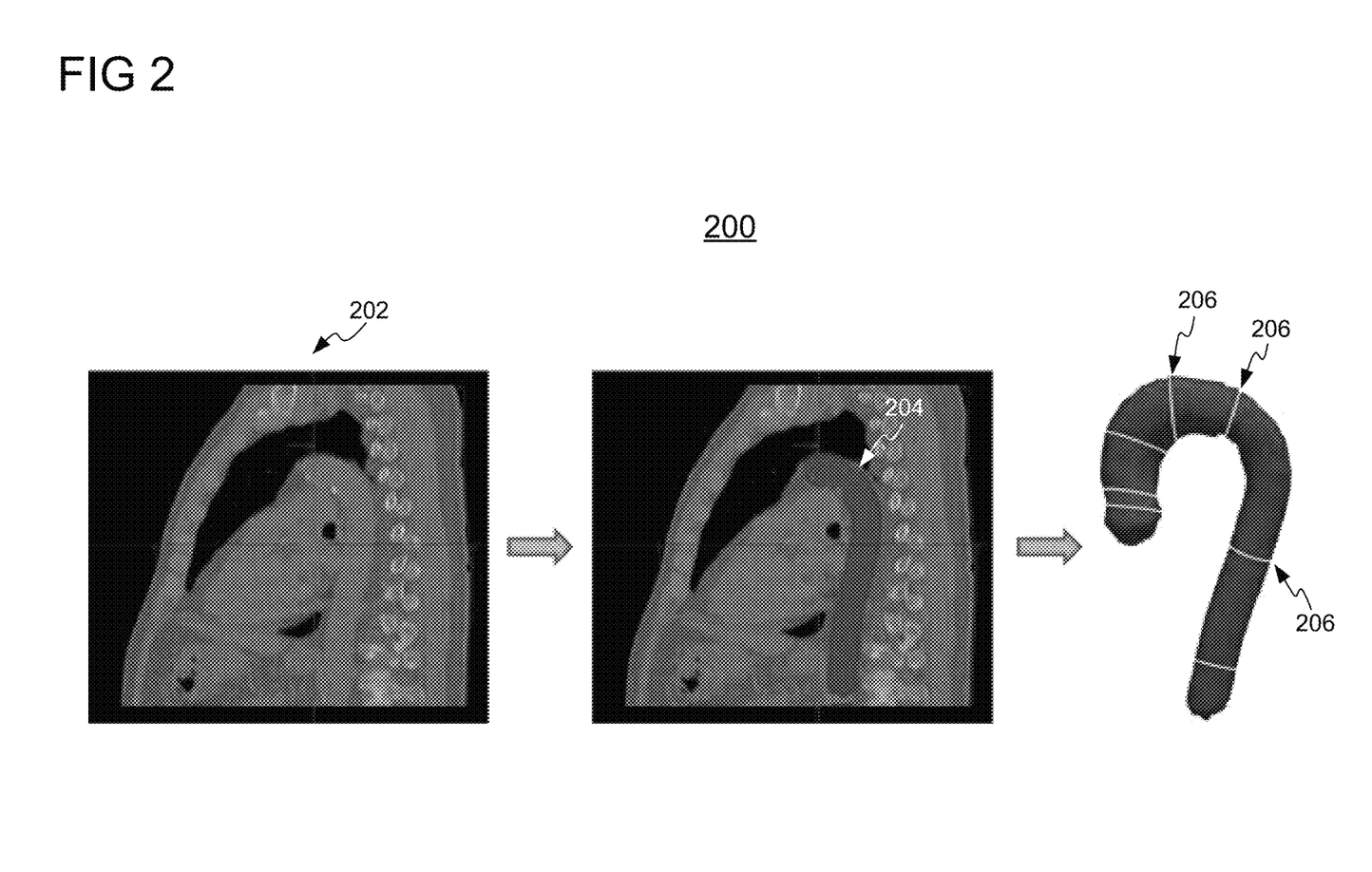
FIG. 2 shows a high-level workflow for evaluating an aorta of a patient, in accordance with one or more embodiments.

FIG. 2 shows a high-level workflow 200 for evaluating an aorta of a patient, in accordance with one or more embodiments. In workflow 200, a CT medical image 202 of a chest of a patient is acquired. Aorta 204 is segmented from medical image 202. A plurality of measuring planes 206 are identified on segmented aorta 204. At each measuring plane 206, one or more diameters of segmented aorta 204 are calculated. The one or more diameters may be compared to a normal range of diameters for the patient to evaluate the aorta. For example, diameters outside the normal range may indicate abnormalities in the aorta. Workflow 200 thereby provides automatic detection and quantification of the aorta of the patient.

Figure 3:
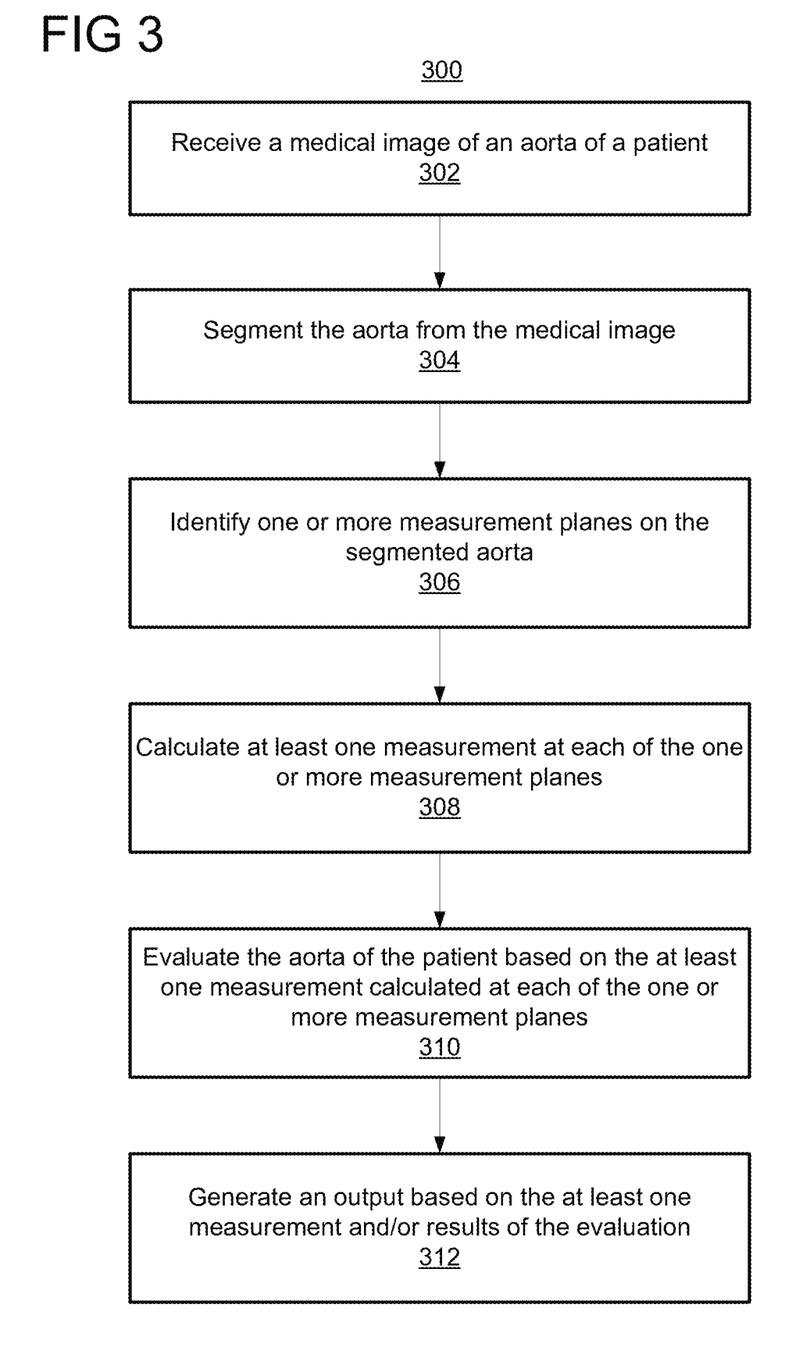
FIG. 3 shows a method for evaluating an aorta of a patient, in accordance with one or more embodiments.

FIG. 3 shows a method 300 for evaluating an aorta of a patient, in accordance with one or more embodiments. Method 300 will be discussed with respect to system 100 of FIG. 1. In one embodiment, the steps of method 300 are performed by workstation 102 of FIG. 1.

At step 302, a medical image of an aorta of a patient is received. The aorta in the medical image may be an entire aorta of the patient or a portion of the aorta of the patient. The medical image may be directly received from a medical imaging system, such as, e.g., medical imaging system 104 of FIG. 1. Alternatively, the medical image may be received by loading a previously acquired medical image from storage or memory of a computer system or receiving a medical image that has been transmitted from a remote computer system. In one embodiment, the medical image is a CT medical image, however it should be understood that the medical image may be of any suitable modality.

At step 304, the aorta is segmented from the medical image. The aorta may be segmented from the medical image using any suitable approach. In one embodiment, the aorta is segmented from the medical image by applying a deep learning model. The deep learning model may be, for example, a deep image-to-image network. In one embodiment, the deep learning model is trained and applied as described in further detail below with respect to FIG. 4. In one embodiment, the aorta is segmented from the medical image using the method described in U.S. Pat. No. 9,715, 637, the disclosure of which is incorporated by reference herein in its entirety. The segmented aorta may be represented, e.g., as a mesh of the aorta in the medical image, as a mask assigning labels to each voxel of the medical image, as a point cloud of points belonging to the aorta in the medical image, or in any other suitable format.

At step 306, one or more measurement planes are identified on the segmented aorta. The measurement planes are cross-sectional planes on the aorta at locations of interest where measurements are to be obtained. In one embodiment, the locations of interest of the measurement planes are predefined landmarks on the aorta. For example, the locations of interest of the measurement planes may be clinically significant locations on the aorta according to clinically accepted guidelines. Examples of such clinically significant locations of interest of the measurement planes include the aortic annulus, aortic root, sinotubular junction, tube, aortic arch, descending aorta, and abdominal aorta.

The one or more measurement planes may be identified based on the medical image, the segmented aorta, an aortic centerline of the aorta, and/or other anatomical information of the patient using any suitable approach. For example, the one or more measurement planes may be identified using trained deep learning models or other simpler model-based techniques. The one or more measurement planes may be provided as a location on the aortic centerline (e.g., a point on the aortic centerline) with a plane normal vector.

In some embodiments, the models may be unable to identify the locations of interest for the one or more measurement planes due to, e.g., noise or other imaging artifacts. In such cases, a separate deep learning model may be used to predict the locations of interest using other available information.

The aortic centerline of the aorta may be computed by applying a trained deep learning model, however any suitable approach may be employed. In one embodiment, the aorta is segmented from the medical image and the aortic centerline is computed for the aorta in a joint and iterative process to increase the accuracy of both, as described below in further detail with respect to FIG. 5.

The anatomical information of the patient used to identify the one or more measurement planes may include features of the patient such as, e.g., location and size of the heart, location of nearby anatomical landmarks (e.g., lungs, spine, aortic bifurcation, and subclavian arteries), etc. The anatomical information of the patient may be extracted from the medical image, e.g., by applying separate deep learning networks trained to identify such anatomical information.

The anatomical information of the patient may be in any suitable format. For example, the anatomical information of the patient may be represented as denoting the location of different landmarks, meshes or masks denoting the boundary of specific organs, feature vectors embedding information about the medical image, etc.

In one embodiment, instead of identifying the one or more measurement planes from the segmented aorta (segmented at step 304), the one or more measurement planes are directly identified from the medical image received at step 302 and step 304 is skipped.

Figure 6:
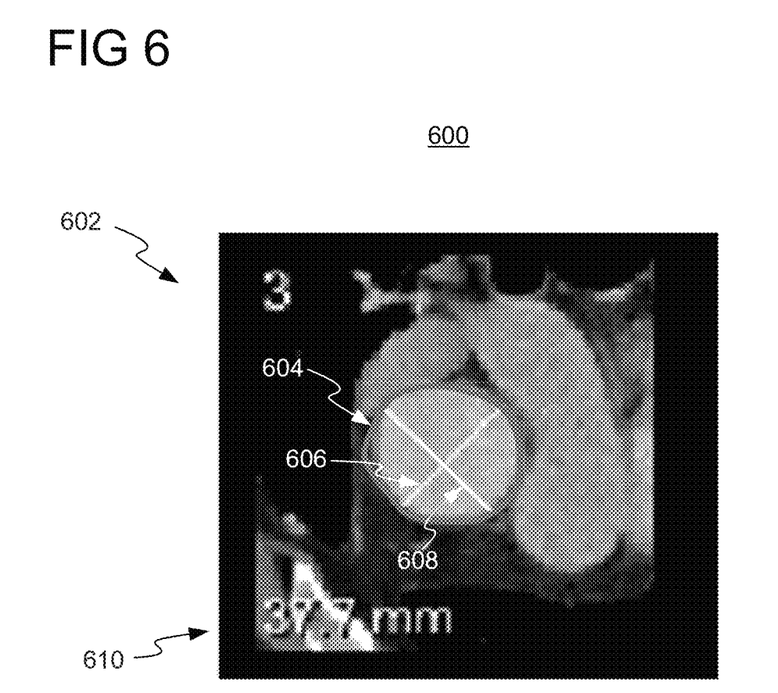
FIG. 6 shows an illustrative user interface depicting measurements and results of an evaluation of an aorta, in accordance with one or more embodiments.

At step 308, at least one measurement is calculated at each of the one or more measurement planes to evaluate the aorta. The at least one measurement may include a diameter of the segmented aorta, however any other suitable measurement may be calculated. In one embodiment, a plurality of diameters is calculated at different directions for each measurement plane. For example, the at least one measurement may include a maximum, a minimum, and/or an average diameter for each measurement plane. In one embodiment, the at least one measurement includes the maximum diameter and the diameter along a direction orthogonal to the maximum diameter for each measurement plane. FIG. 6 shows an example of measurements taken at different directions on a measurement plane, as discussed in more detail below.

The at least one measurement may be calculated using any suitable approach. In one embodiment, a deep learning model is trained to predict the at least one measurement. In one embodiment, along with predicting the at least one measurement, the machine learning model may also predict a degree of uncertainty corresponding to the predicted at least one measurement. The at least one measurement may be compared with measurements from a training dataset and, where the at least one measurement deviates (e.g., by a threshold amount) from the measurements from the training dataset, user confirmation or intervention is requested. Actions taken by the user can be saved and applied as training data for improving the model for future datasets.

At step 310, the aorta of the patient is evaluated based on the at least one measurement calculated at each of the one or more measurement planes. In one embodiment, the at least one measurement calculated at each of the one or more measurement planes is compared with a respective range such that measurements outside the range may indicate abnormality of the aorta. For example, diameters of the aorta of the patient for a measurement plane may be compared with a patient-specific normal range of aortic diameters for that measurement plane. The patient-specific normal range of aortic diameters may be determined based on the patient, such as, e.g., the age of the patient, the gender of the patient, the ethnicity of the patient, and other demographic factors of the patient. The patient-specific normal range of aortic diameters may be a clinically accepted range of aortic diameters, e.g., based on American Heart Association or European Society of Cardiology guidelines. Accordingly, a patient-specific normal range of aortic diameters may be defined for each of the one or more measurement planes to detect locations of interest where the aortic diameter of the patient is outside of the patient-specific normal range.

At step 312, an output is generated based on results of the at least one measurement (calculated at step 308) and/or the evaluation of the aorta (performed at step 310). In one embodiment, the output is generated by causing the results of the at least one measurement and/or the evaluation of the aorta to be displayed on a display device of a computer system, storing the results of the at least one measurement and/or the evaluation of the aorta on a memory or storage of a computer system, or by transmitting the results of the at least one measurement and/or the evaluation of the aorta to a remote computer system. FIG. 6 shows an exemplary output comprising a display of a cross-sectional view of an aorta at a measurement plane and two orthogonal diameters of the aorta, as discussed in further detail below.

The calculated measurements may be displayed to a user on a display device in any suitable format. In one example, photorealistic rendering techniques can be used to generate a high-resolution image of the aorta, while also depicting additional information, such as, e.g., the one or more measurement planes, the at least one measurement (e.g., average diameter), and results of the evaluation. In another example, the segmented aorta, aortic centerline, and locations of the one or more measurement planes may be shown overlaid on top of the originally received medical image in a curved multiplanar reconstruction (MPR) view. The MPR view has the advantage of showing the segmented aorta and the one or more measurement planes in relation to other anatomical structures of importance, such as, e.g., the brachiocephalic artery, the left carotid and subclavian arteries, etc. In one embodiment, the one or more measurement planes are only on the aortic trunk while a larger subset of the aorta is displayed.

In one embodiment, the output comprises an audio and/or visual alert generated in response to results of the evaluation of the aorta to alert a user of the results. For example, the alert may alert the user that the at least one measurement is outside the patient-specific normal range for the patient. In one example, the alert may include a popup window notifying the user of the results of the evaluation and prompting the user to confirm the results of the evaluation. In response, the user may correct, for example, the segmentation of the aorta, the aortic centerline, the location and/or orientation of the one or more measurement planes, and/or the at least one measurement. The user actions may be saved and used as training data to improve the model for future predictions.

In one embodiment, a risk score is calculated indicating a likelihood of adverse outcomes. The risk score may be calculated, e.g., in response to results of the evaluation or in response to the user confirming the alert. Based on the calculated risk score and clinical guidelines, a clinical treatment plan for optimal patient outcome may be suggested. For instance, the clinical treatment plan may include a follow-up evaluation with the duration based on the degree of severity indicated by the risk score, potential additional testing (e.g., additional imaging or laboratory tests) to confirm the results, or immediate intervention where the risk score indicates high risk. The clinical treatment plan may be based on established clinical guidelines, and presented to the user with a link to published clinical decision making pathways supporting the plan along with known statistics of the different risks and outcomes associated with each item in the plan. In one embodiment, the clinical treatment plan may be sent to a patient management system to automatically trigger communication with the patient to facilitate execution of the clinical treatment plan (e.g., to facilitate setting up an appointment).

The steps of method 300 can be performed fully automatic and/or semi-automatic. In the fully automatic case, the models automatically perform all steps and generate results without additional user input. The results can be in any suitable format. In one embodiment, the results are in a format that can be directly entered into a hospital data management system. In the semi-automatic case, the outputs of the models (e.g., the segmentation of the aorta, the identification of the location/orientation of the one or more measurement planes, and/or the calculation of the at least one measurement, etc.) can be edited by the user. For example, over-segmentation of the aorta at step 304 can be corrected by the user. The corrected results may be entered into the hospital management system. The user input may be saved and applied as training data to improve future predictions.

In some embodiments, the machine learning model trained to predict a certain result, such as, e.g., segmentation of the aorta or calculation of the at least one measurement, may provide inaccurate results due to noise or artifacts in portions of the medical image. Instead of providing inaccurate results, a user may be prompted to manually enter or correct the results.

Figure 4:
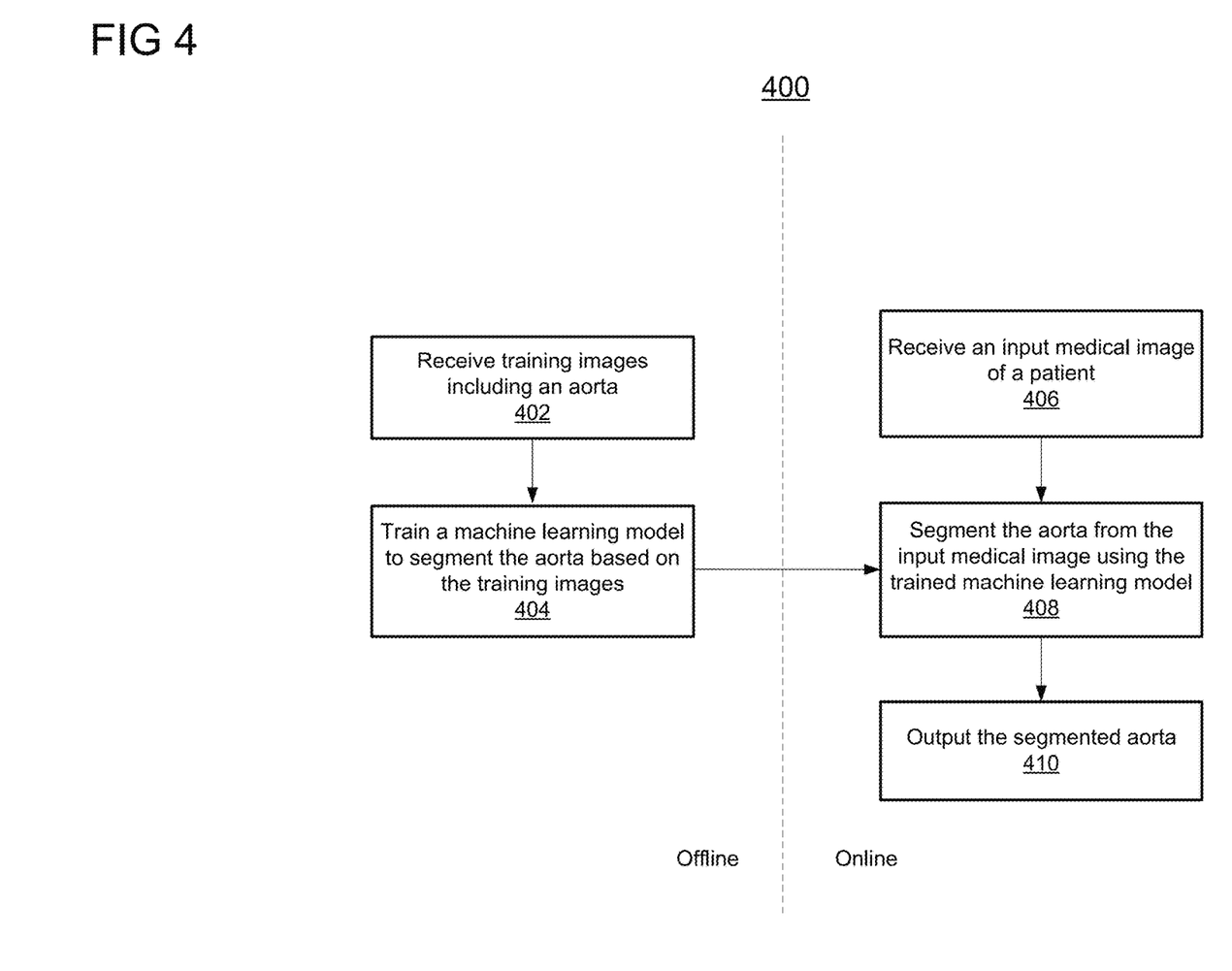
FIG. 4 shows a workflow for training and applying a machine learning model for segmenting an aorta from a medical image, in accordance with one or more embodiments.

FIG. 4 shows a workflow 400 for training and applying a machine learning model for segmenting an aorta from a medical image, in accordance with one or more embodiments. Steps 402-404 show an offline or training stage for training a machine learning model. Steps 406-410 show an online or inference stage for applying the trained machine learning model on newly received input medical images. In one embodiment, step 304 of FIG. 3 is performed by performing the steps of the inference state (steps 406-410). The inference stage (steps 406-410) can be repeated for each newly received input medical image(s).

At step 402, during a training stage, training images including an aorta are received. The training images are medical images in a modality corresponding to the modality of the input medical image to be analyzed during the inference stage (at step 406). For example, the modality may be computed tomography (CT), magnetic resonance (MR), DynaCT, ultrasound, x-ray, positron emission tomography (PET), etc. In one embodiment, the training images can be received by loading a number of previously stored medical training images from a database of medical images.

The training images may comprise real training images annotated to indicate the location of the aorta. The annotations may be in any suitable form. In one embodiment, the annotations comprise, e.g., a mesh, a mask assigning a label to each voxel in the training images, or a point cloud of points belonging to the aorta in the training images.

The training images may also comprise synthetic training images. The synthetic images may be generated using, e.g., imaging of phantom datasets or imaging simulators, which generate synthetic images based on the size and location of different organs. In some embodiments, the synthetic images are generated using deep learning models, such as, e.g., a generative adversarial network (GAN) trained to generate realistic looking images using known images from other imaging modalities. For example, a GAN may be trained to generate CT training images of the aorta from MRI images. This model may be used to produce a large set of training images.

The training images may further comprise augmented training images generated using data augmentation techniques. In one embodiment, the augmented training images may be generated by applying transformations to real training images and their annotations. Any suitable transformation may be applied, such as, e.g., adding a degree of noise to the real training images, scaling the real training image, rotating the real training image, etc. In one embodiment, the transformations are locally varied to simulate pathologies or conditions. For example, the real training images and their annotations may be locally dilated to simulate the effect of an abdominal aneurysm. Other transformations may be applied to simulate, e.g., an aortic stenosis.

In one embodiment, the training images may be associated with additional data for training the machine learning model. For example, the additional data associated with the training images may include the additional anatomical information, as described above with respect to step 306 of FIG. 3. In another example, the additional data associated with the training images may also include a genetic profile of a patient associated with the training image.

In one embodiment, the training images include an input image previously received during the inference stage where the user have provided input (e.g., to define the segmentation). Accordingly, the user input is provided as the ground truth for the input image. The input image may be from a local population of a healthcare center so that the model learns to adapt better to the population of the healthcare center, or from a global population of all (or a plurality of) healthcare centers received from a remote location to improve the future performance of those healthcare centers.

At step 404, a machine learning model is trained to segment an aorta from a medical image based on the training images (and additional data). In one embodiment, the machine learning model is a deep image-to-image network, which is trained to learn the correspondence between the training images and their ground truths. The deep image-to-image network learns to minimize the difference between the predicted segmentation (e.g., the segmentation mask) and the ground truth (e.g., the ground truth mask), which can be accomplished using different mathematical loss functions (e.g., known loss functions).

At step 406, during an inference stage, an input medical image of a patient is received. The input medical image comprises an aorta. Additional data may also be received, such as, e.g., additional anatomical information of the patient, genetic profile information of the patient, etc. In one embodiment, the input medical image is the medical image received at step 302 of FIG. 3.

At step 408, a segmentation of the aorta from the input medical image is predicted using the trained machine learning model. The input medical image is input to the trained machine learning model, and the trained machine learning model generates the segmentation of the aorta based on the input medical image. In some embodiments, the additional patient data, such as additional anatomical information of the patient, genetic profile information of the patient, etc., may also be input to the trained machine learning model and used to generate the segmentation of the aorta. The segmentation may be in any suitable form, such as, e.g., a mesh of the aorta in the input medical image, a mask assigning labels to each voxel of the input medical image, or a point cloud of points belonging to the aorta in the input medical image.

At step 410, the segmentation of the aorta is output. In one embodiment, the segmentation of the aorta is output by returning the segmentation to step 304 of FIG. 3. In some embodiments, the segmentation of the aorta can be output by displaying the segmentation on a display device of a computer system, storing the segmentation on a memory or storage of a computer system, or by transmitting the segmentation to a remote computer system.

It should be understood that once the machine learning model is trained during the training stage, the steps 406-410 of the inference stage can be repeated for each newly received input medical image(s).

It should further be understood that workflows similar to workflow 400 can be performed to train and apply a machine learning model to perform tasks described herein using suitable training data. For example, workflows similar to workflow 400 can be performed to train and apply a machine learning model to compute an aortic centerline, to identify the additional anatomical information, and to identify the one or more measurement planes at step 306 of FIG. 3, to calculate the at least one measurement at step 308 of FIG. 3, or to generate synthetic images in step 402 of FIG. 4 using suitable training data.

Figure 5:
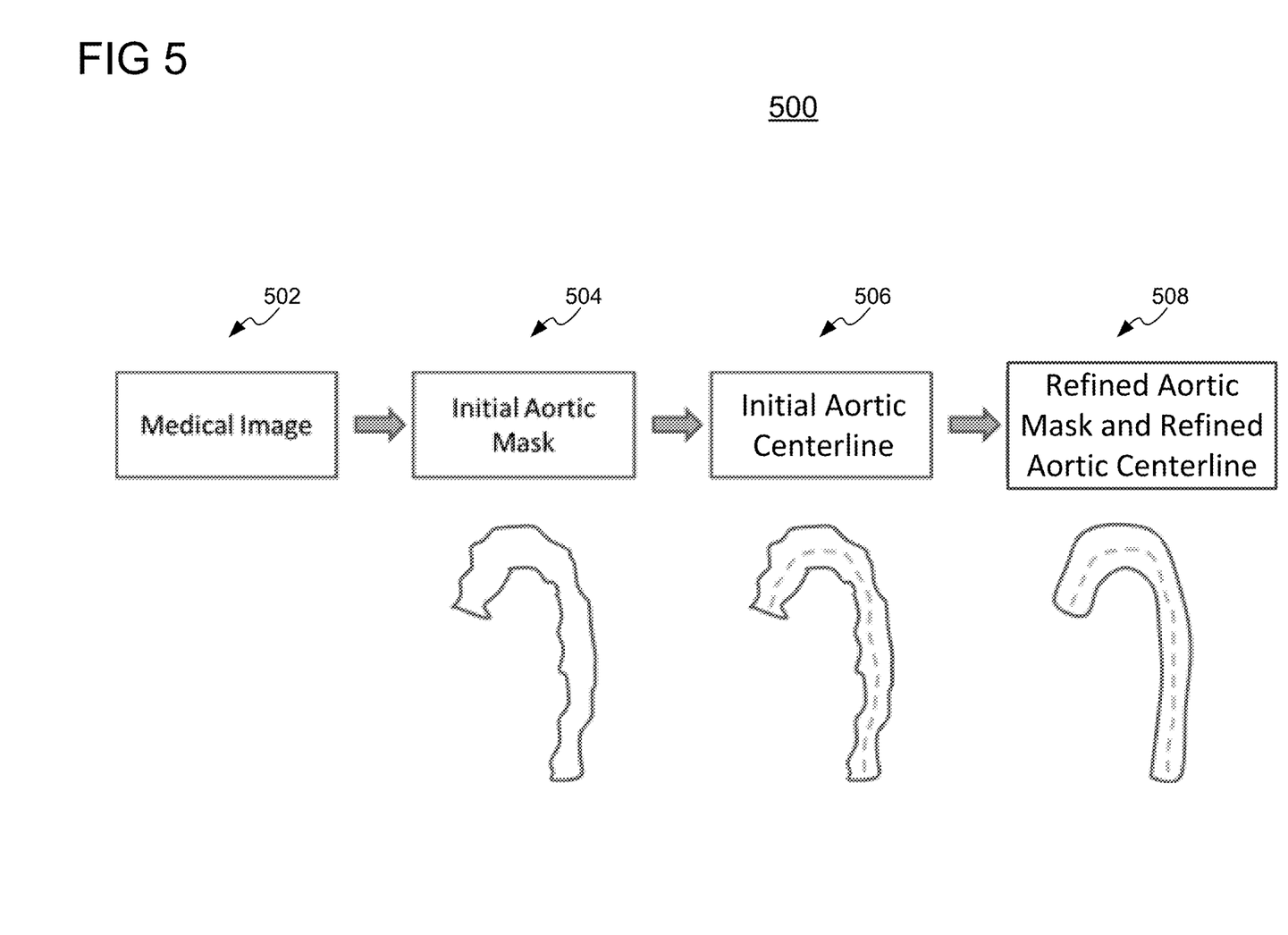
FIG. 5 shows a workflow of a joint and iterative process for segmenting an aorta from a medical image and computing an aortic centerline of the aorta, in accordance with one or more embodiments.

FIG. 5 shows a workflow 500 of a joint and iterative process for segmenting an aorta from a medical image and computing an aortic centerline of the aorta, in accordance with one or more embodiments. In one embodiment, workflow 500 may be performed to segment the aorta from the medical image at step 304 of FIG. 3 and to compute the aortic centerline of the aorta at step 306 of FIG. 3. Advantageously, the joint and iterative process of workflow 500 provides a more accurate segmented aorta and aortic centerline.

At step 502, a medical image including an aorta is received.

At step 504, the aorta is segmented from the medical image to provide an initial aortic mask. For example, the aorta may be segmented from the medical image using a trained machine learning model, as trained and applied according to FIG. 4. While the segmented aorta is represented as an aortic mask at step 504, it should be understood that the segmented aorta may be represented in any suitable format (e.g., a mesh or a point cloud).

At step 506, an initial aortic centerline of the aorta is computed. The aortic centerline may be computed using any suitable approach, such as a trained deep learning model.

At step 508, a refined aortic mask and a refined aortic centerline are determined. In one embodiment, the refined aortic mask may first be determined by refining the initial aortic mask using a region-wise model applied in the neighborhood of the initial aortic centerline. The refined aortic centerline may then be determined using, e.g., a trained deep learning model based on the refined aortic mask. Step 508 may be iteratively repeated any number of times (e.g., a predetermined number of times) until a suitable segmentation of the aorta and aortic centerline are determined.

It should be understood that steps 504 and 506 may be performed in any order. For example, in one embodiment, an initial aortic centerline is first computed directly from the medical image at step 506 and then an initial aortic mask is determined from the medical image based on the initial aortic centerline at step 504. Accordingly, in this embodiment, at step 508, a refined aortic centerline is first determined using a trained deep learning model based on the initial aortic mask and a refined aortic mask is then determined using the region-wise model based on the refined aortic centerline.

FIG. 6 shows a user interface 600 depicting measurements and results of an evaluation of an aorta, in accordance with one or more embodiments. In one embodiment, user interface 600 may be an output at step 312 of FIG. 3. User interface 600 shows a CT medical image 602 depicting a cross-sectional view of an aorta at a measurement plane. A segmented aortic mask 602 is overlaid thereon with measurements 606 and 608 representing orthogonal diameters of segmented aortic mask 602 that were calculated. Measurement result 610 is shown indicating a diameter of 37.7 millimeters for measurement 608.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIGS. 2-5. Certain steps or functions of the methods and workflows described herein, including one or more of the steps or functions of FIGS. 2-5, may be performed by a server or by another processor in a network-based cloud-computing system. Certain steps or functions of the methods and workflows described herein, including one or more of the steps of FIGS. 2-5, may be performed by a client computer in a network-based cloud computing system. The steps or functions of the methods and workflows described herein, including one or more of the steps of FIGS. 2-5, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIGS. 2-5, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 7:
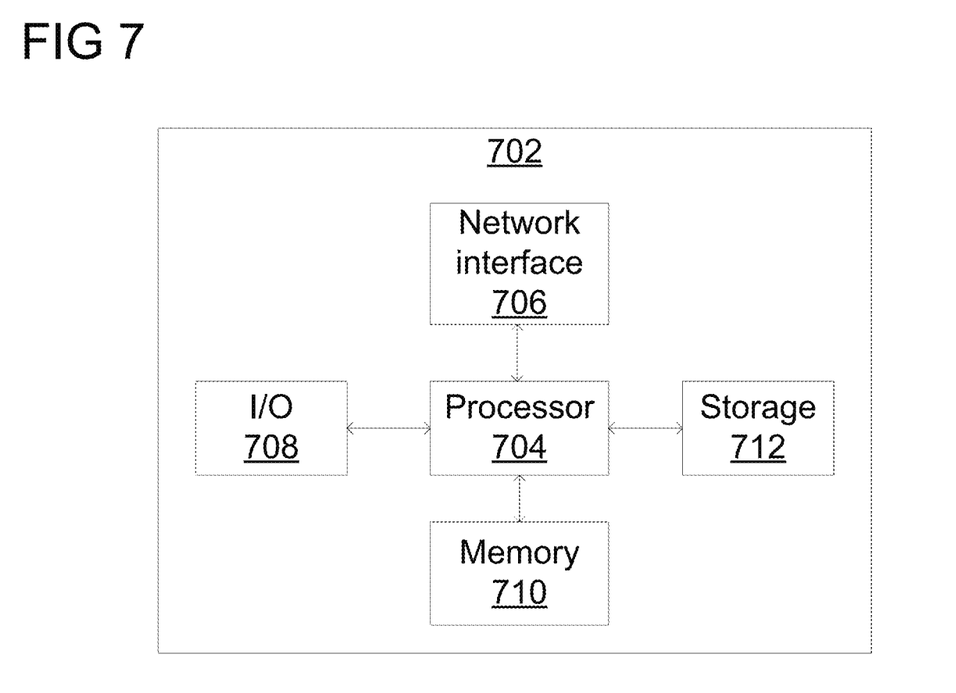
FIG. 7 shows a high-level block diagram of a computer.

A high-level block diagram of an example computer 702 that may be used to implement systems, apparatus, and methods described herein is depicted in FIG. 7. Computer 702 includes a processor 704 operatively coupled to a data storage device 712 and a memory 710. Processor 704 controls the overall operation of computer 702 by executing computer program instructions that define such operations.

The computer program instructions may be stored in data storage device 712, or other computer readable medium, and loaded into memory 710 when execution of the computer program instructions is desired. Thus, the method and workflow steps or functions of FIGS. 2-5 can be defined by the computer program instructions stored in memory 710 and/or data storage device 712 and controlled by processor 704 executing the computer program instructions. For example, the computer program instructions can be implemented as computer executable code programmed by one skilled in the art to perform the method and workflow steps or functions of FIGS. 2-5. Accordingly, by executing the computer program instructions, the processor 704 executes the method and workflow steps or functions of FIGS. 2-5. Computer 704 may also include one or more network interfaces 706 for communicating with other devices via a network. Computer 702 may also include one or more input/output devices 708 that enable user interaction with computer 702 (e.g., display, keyboard, mouse, speakers, buttons, etc.).

Processor 704 may include both general and special purpose microprocessors, and may be the sole processor or one of multiple processors of computer 702. Processor 704 may include one or more central processing units (CPUs), for example. Processor 704, data storage device 712, and/or memory 710 may include, be supplemented by, or incorporated in, one or more application-specific integrated circuits (ASICs) and/or one or more field programmable gate arrays (FPGAs).

Data storage device 712 and memory 710 each include a tangible non-transitory computer readable storage medium. Data storage device 712, and memory 710, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 708 may include peripherals, such as a printer, scanner, display screen, etc. For example, input/output devices 708 may include a display device such as a cathode ray tube (CRT) or liquid crystal display (LCD) monitor for displaying information to the user, a keyboard, and a pointing device such as a mouse or a trackball by which the user can provide input to computer 702.

Any or all of the systems and apparatus discussed herein, including elements of workstation 102 of FIG. 1, may be implemented using one or more computers such as computer 702.

One skilled in the art will recognize that an implementation of an actual computer or computer system may have other structures and may contain other components as well, and that FIG. 7 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for evaluating an aorta of a patient, comprising:
    receiving a medical image of an aorta of a patient;
    segmenting the aorta from the medical image by iteratively refining 1) an aortic mask of the aorta based on an aortic centerline of the aorta and 2) the aortic centerline based on the aortic mask;
    identifying one or more measurement planes on the segmented aorta based on the aortic centerline;
    calculating a maximum diameter of the segmented aorta and a diameter of the segmented aorta along a direction orthogonal to the maximum diameter at each of the one or more measurement planes; and
    evaluating the aorta of the patient by comparing the maximum diameter and the diameter along the direction orthogonal to the maximum diameter calculated at each respective measurement plane of the one or more measurement planes with a patient-specific range of normal aortic diameters defined for the respective measurement plane.

2. The method of claim 1, wherein identifying one or more measurement planes on the segmented aorta based on the aortic centerline comprises:
    identifying the aortic centerline of the aorta; and
    identifying one or more locations on the aortic centerline and corresponding plane normal vectors as the one or more measurement planes.

3. The method of claim 1, further comprising
    calculating at least one of a minimum diameter and an average diameter of the segmented aorta at each of the one or more measurement planes.

4. The method of claim 1, further comprising:
    generating an alert indicating results of the evaluating in response to the comparing.

5. The method of claim 1, further comprising:
    calculating a risk score in response to the comparing; and
    causing a clinical treatment plan to be presented to a user based on the risk score.

6. The method of claim 1, further comprising:
    causing results of the calculating and/or the evaluating to be displayed on a display device.

7. An apparatus for evaluating an aorta of a patient, comprising:
    means for receiving a medical image of an aorta of a patient;
    means for segmenting the aorta from the medical image by iteratively refining 1) an aortic mask of the aorta based on an aortic centerline of the aorta and 2) the aortic centerline based on the aortic mask;
    means for identifying one or more measurement planes on the segmented aorta based on the aortic centerline;
    means for calculating a maximum diameter of the segmented aorta and a diameter of the segmented aorta along a direction orthogonal to the maximum diameter at each of the one or more measurement planes; and
    means for evaluating the aorta of the patient by comparing the maximum diameter and the diameter along the direction orthogonal to the maximum diameter calculated at each respective measurement plane of the one or more measurement planes with a patient-specific range of normal aortic diameters defined for the respective measurement plane.

8. The apparatus of claim 7, wherein the means for identifying one or more measurement planes on the segmented aorta based on the aortic centerline comprises:
means for identifying the aortic centerline of the aorta; and
means for identifying one or more locations on the aortic centerline and corresponding plane normal vectors as the one or more measurement planes.

9. The apparatus of claim 7, further comprising
means for calculating at least one of a minimum diameter and an average diameter of the segmented aorta at each of the one or more measurement planes.

10. A non-transitory computer readable medium storing computer program instructions for evaluating an aorta of a patient, the computer program instructions when executed by a processor cause the processor to perform operations comprising:
receiving a medical image of an aorta of a patient;
segmenting the aorta from the medical image by iteratively refining 1) an aortic mask of the aorta based on an aortic centerline of the aorta and 2) the aortic centerline based on the aortic mask;
identifying one or more measurement planes on the segmented aorta based on the aortic centerline;
calculating a maximum diameter of the segmented aorta and a diameter of the segmented aorta along a direction orthogonal to the maximum diameter at each of the one or more measurement planes; and
evaluating the aorta of the patient by comparing the maximum diameter and the diameter along the direction orthogonal to the maximum diameter calculated at each respective measurement plane of the one or more measurement planes with a patient-specific range of normal aortic diameters defined for the respective measurement plane.

11. The non-transitory computer readable medium of claim 10, wherein identifying one or more measurement planes on the segmented aorta based on the aortic centerline comprises:
identifying the aortic centerline of the aorta; and
identifying one or more locations on the aortic centerline and corresponding plane normal vectors as the one or more measurement planes.

12. The non-transitory computer readable medium of claim 10, the operations further comprising:
generating an alert indicating results of the evaluating in response to the comparing.

13. The non-transitory computer readable medium of claim 10, the operations further comprising:
calculating a risk score in response to the comparing; and
causing a clinical treatment plan to be presented to a user based on the risk score.

14. The non-transitory computer readable medium of claim 10, the operations further comprising:
causing results of the calculating and/or the evaluating to be displayed on a display device.

* * * * *